United States Patent [19]

Scheunemann

[11] Patent Number: 4,904,264
[45] Date of Patent: Feb. 27, 1990

[54] ARTIFICAL JOINT SYSTEM

[75] Inventor: Rüdiger Scheunemann, Lohmar-Donrath, Fed. Rep. of Germany

[73] Assignee: Fried. Krupp GmbH, Essen, Fed. Rep. of Germany

[21] Appl. No.: 795,493
[22] PCT Filed: May 4, 1985
[86] PCT No.: PCT/EP85/00197
 § 371 Date: Oct. 24, 1985
 § 102(e) Date: Oct. 24, 1985
[87] PCT Pub. No.: WO85/05027
 PCT Pub. Date: Nov. 21, 1985

[30] Foreign Application Priority Data

May 8, 1984 [DE] Fed. Rep. of Germany ....... 3416872
 May 29, 1984 [DE] Fed. Rep. of Germany ....... 3420035
 Jun. 27, 1984 [DE] Fed. Rep. of Germany ....... 3423667

[51] Int. Cl.$^4$ .............................................. A61F 2/30
[52] U.S. Cl. ................................................... 623/18
[58] Field of Search ................................. 623/16–23; 128/924

[56] References Cited

U.S. PATENT DOCUMENTS 4,089,071 5/1978 Kalnberz et al. ............... 128/924 Z
4,532,660 8/1985 Field ..................................... 623/23

FOREIGN PATENT DOCUMENTS 0010527 4/1980 European Pat. Off. .............. 623/20
23608 2/1981 European Pat. Off. .
24008 2/1981 European Pat. Off. .
71242 2/1983 European Pat. Off. .
99167 1/1984 European Pat. Off. .
2620907 11/1977 Fed. Rep. of Germany .
2854334 6/1980 Fed. Rep. of Germany .
995762 12/1951 France .
0581936 11/1977 U.S.S.R. ................................. 623/16
0581938 11/1977 U.S.S.R. ................................. 623/16

Primary Examiner—Richard J. Apley
Assistant Examiner—David J. Isabella
Attorney, Agent, or Firm—Spencer & Frank

[57] ABSTRACT

The invention relates to an artificial joint system which, by a combination of defined pretension in the implant in the resection plane and a wholly or partially resorbable shaft or clamping system connects, after a transition period after implantation, the intermediate member of the implant with the remaining bone in the resection plane and the shaft required in the long bone during the transition period decomposes at the surface or the clamping system of the intermediate member deomposes to such an extent that unphysiological force transmission into the bone through the shaft of the implant or through the clamping system is no longer possible.

31 Claims, 3 Drawing Sheets

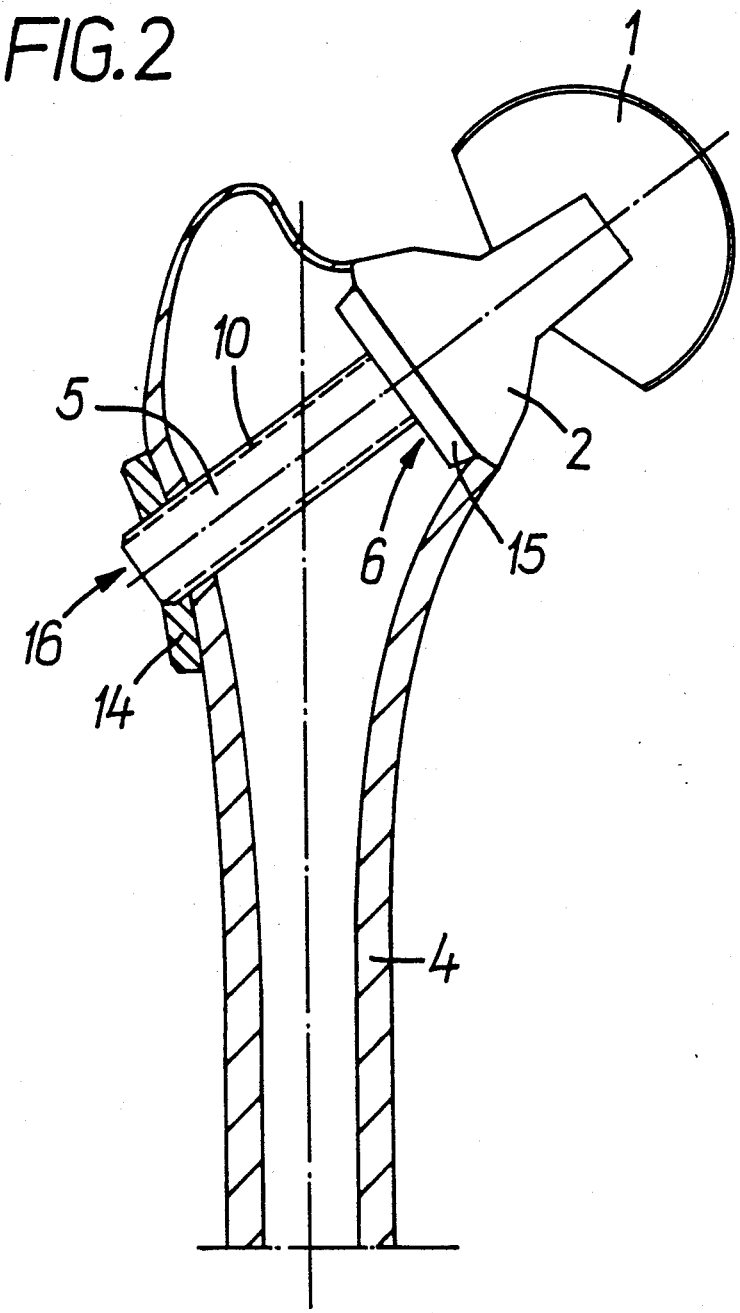

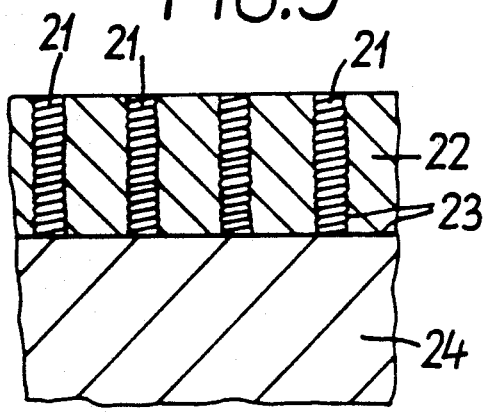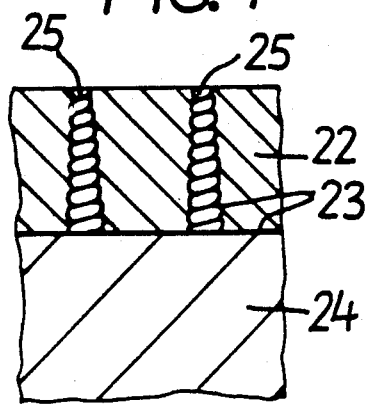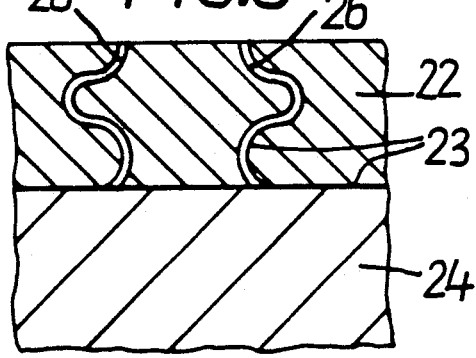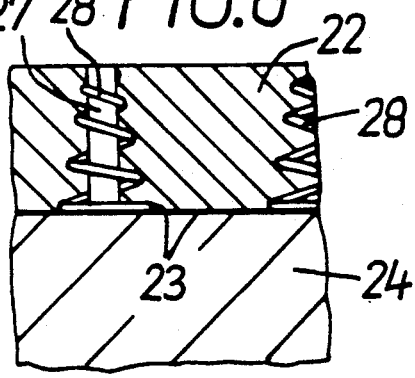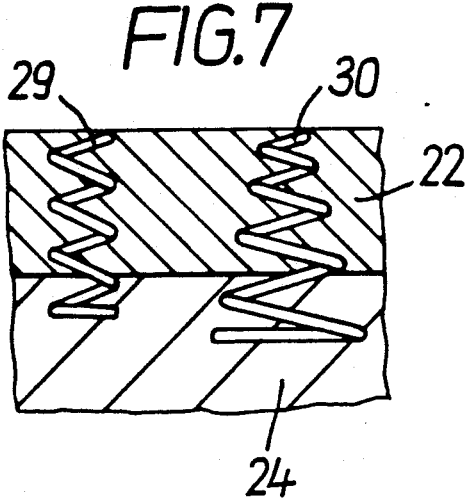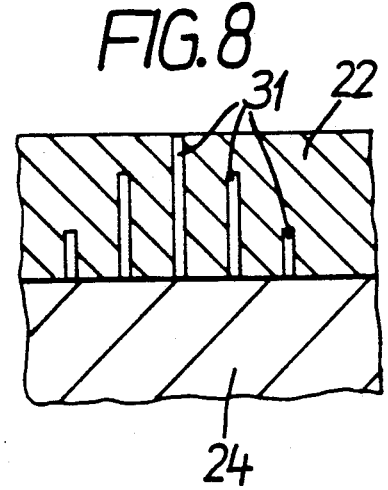

ARTIFICAL JOINT SYSTEM

BACKGROUND OF THE INVENTION

1. Field of the Invention

The invention relates to an artificial joint system for cement-free implantation, the system including an implant and a clamping device and is suitable, for example, for artificial hip joints, artificial knee joints and artificial elbow joints. This invention covers, in particular, those joint systems which include an intermediate member (bone shaft member) extending in the direction of the bone shaft and supporting a joint head associated with a joint socket and a clamping device with which the intermediate member can be pressed to the bone in the resection plane. The clamping device is understood to also include, in particular, a shaft extending in the longitudinal direction of the long bone and being placeable into a bore of the long bone, the shaft having a head section provided with a threaded bore extending perpendicularly to the resection plane into which bore the intermediate member is screwed. The invention further relates to a method for implanting such a joint system.

2. Background of the Art

It is known that numerous structures of different design are used as artificial joint prostheses. For example, German Pat. No. 2,854,334 discloses a femur-hip joint endoprosthesis which, particularly in the head section of the shaft, has a fill bore into which the spongy tissue can be inserted so as to reach the exterior of the shaft through perforations and thus assure secure growth around the endoprosthesis. In this shaft prosthesis, as well as in the other prior art shaft prostheses with and without collar, there is a greater or lesser amount of unphysiological introduction of force into the long bone, either due to unphysiological radial stresses in the shaft prostheses or due to changes in longitudinal stresses in the long bone, for example, as a result of pretension. Moreover, the prior art clamping systems result in unphysiological introductions of force at the side of the long bone opposite the resection plane and thus result in fault-inducing stresses on the bone. In all prior art artificial joint systems, this results in limited durability which, on the average, today lies between five and ten years.

SUMMARY OF THE INVENTION

It is the object of the invention to provide an artificial joint system and a method for implanting it, as well as a surgical instrument with which the natural flow of forces in the long bone can be completely restored after healing. In particular, a durable and life-long bond or anchorage, respectively, of the artificial joint system with the natural bone is to be assured to thus prevent or completely avoid repetitive surgery in connection with implantations.

This is accomplished in that the clamping device and particularly the shaft are wholly or partially resorbable and the bone's resection plane joins specifically the contact portion of the implant or of the intermediate member have a surface which enhances growth into the bone. An implant including an intermediate member is preferably inserted in such a manner that, in the resection plane, the implant rests medially on the cortex under pretension.

Advantageously, a combination is thus provided of a defined pretension in the implant in the resection plane and a wholly or partially resorbable shaft or clamping system so that, after a transition period after implantation, the intermediate member or the contact member of the implant joins itself with the remainder of the bone in the resection plane and the shaft required in the long bone for the transition period is decomposed at its surface, or the clamping system of the intermediate member is decomposed to such an extent that unphysiological force transmissions through the shaft of the implant or through the clamping system into the bone are no longer possible. Advantageously, this artificial joint system can be used for all long bones, i.e. for artificial hip joints, artificial knee joints, artificial elbow joints, etc. While in its first phase after surgery, pretension between the implant and the remainder of the bone in the resection plane and a connection of the shaft or generally of a clamping device with the bone produces a reduction of the unphysiological flow of forces, during the second phase after surgery, the natural bone grows together with the implant facing the resection plane so that a firm bond is produced along the resection plane.

According to a further feature of the invention, the clamping device or the shaft, respectively, and the intermediate member are composed entirely or partially of bioactive and/or osteogenesis-inducing material of an inorganic or organic nature or of mixtures thereof. Preferably, tricalcium phosphate, hydroxylapatite and bioglasses are employed. The stated members may also be merely coated with such material; the use of resorbable material being particularly recommended.

In order to increase surface area, it is further possible to provide additional surface structures, e.g. bores or knubs, at the preferably radially symmetrical intermediate member, on its side facing the resection plane so as to enhance ingrowth. Likewise, a central bore in the intermediate member enhances growth of bone tissue into the intermediate member in the resection plane.

Alternatively or in addition to the already mentioned geometric designs, it has been found to be of advantage to have an artificial joint system in which the implant or the intermediate member, respectively, and/or the shaft are provided with a transition structure on the side of the bone and a core composed preferably of a metallic or composite material which is body compatible and can withstand pressure stresses. Flexible metallic wires or flexible fibers, particularly in the form of springs (helixes) and shaped like porcupine quills or brushes are then permanently anchored in the core, extend preferably perpendicularly to the implant surface and are encased by a matrix which is completely or partially resorbable starting in the resection plane. The modulus of elasticity of the wires or fibers is adapted to that of the tissue later to surround the matrix. The use of such a matrix offers advantages also for the shaft, where brush-like fibers and wires penetrate the matrix starting from the core of the shaft.

The described configurations enhance growth of the natural bone in the resection plane around the implant by way of chemical activity and/or by way of surface enlargement of the implant.

If one selects the alternative of surface enlargement in a matrix, further structural features of the invention become possible:

To prevent the wires or fibers from crossing over, which would interfere with the biological growth of bone cells, because then no total inclusion would be assured, the fibers or wires extend without contact, i.e. parallel to one another.

The wires or fibers fixed to the implant core—whether the wires or fibers extend into the core or are fastened to the implant surface by means of an adhesive or are welded or sintered on—are preferably selected in such a manner that, even under all kinds of stresses, such as tension, pressure, bending, torsion and shear forces, they meet two conditions:

1. it is assured that the load is distributed uniformly over the length of the fiber or the wire from the end of the fibers or wires to the implant core;
2. no or only slight micromovement or relative movement is produced between the fibers or wires and the bone or the bone cells. Additionally, the wires and fibers, respectively, increase the area of adhesion between bone and implant.

According to further features of the invention, it is also possible for the wires or fibers to have uniform tension and strength over their length and to project from the implant surface at irregular distances from one another, particularly in groups. In any case, if the wires or fibers are rigidly anchored, after implantation, the fiber or wire arrangement serves to cause them to be wholly or partially enclosed in the bone, free of connective tissue.

According to another feature of the invention, the spacing between the wires or fibers is to be so large that the bone tissue between the individual wires or fibers can be supplied without interference.

Since generally, the wires or fibers absorb and transfer forces only after the bone tissue has grown around them, it is possible, according to a further feature of the invention, to fill the interstices between the wires or fibers with a wholly or partially resorbable bioactive and/or osteogenesis inducing material. The substance introduced into the implant on the side of the bone is resorbed wholly or partially by physiological influence and is replaced by natural bone. Depending on the type of use, the interstices are preferably filled with natural bone substance (spongy tissue). After resorption of the filler material, bone grows without interference around the individual spring-shaped fibers or wires. On the one hand, this increases the area of adhesion between bone and implant and, on the other hand, if the inclusion is effected without connective tissue, the natural bone creates a connection between itself and the implant, even if there is no chemical activity between them.

In wire or fiber configurations still possible within the scope of the above-mentioned characteristics, it is preferable to employ a wire or fiber thickness and/or length of different magnitude, thus making it possible to adapt the wires or fibers with respect to the modulus of elasticity particularly to the bone substance in the resection plane.

According to a further feature of the invention, the structure of the fibers or wires may be helical or wavy. If the helical shape is selected, the helix may be cylindrical, conical or parabolic and may preferably have a pitch which is equal to or greater than the diameter of the helical wire.

For cylindrical helixes, a constant bending stress over their length is accomplished in that the thickness of the helical wire decreases toward the tip of the helix. For conical or parabolic helix cross-sections, the thickness of the helical wire may also be varied. If necessary, it is further possible, in order to absorb shear forces, to provide the helix with a core which is firmly connected with the implant core. Between helix and core there preferably exists no firm connection on the side of the bone.

The materials and geometry of the helix thus adapt the moduli of elasticity between bone tissue and helix by selection of the spring constants. In this way, no micromovement results between spring (helix) and the contacting bone when there are stresses on the bone and on the implant, e.g. alternating bending stresses.

With the wavy fiber or wire structure, uniform strength is realized by different fiber geometries in the fiber itself or with respect to adjacent fibers and by different fiber materials. The fibers or wires, respectively, are preferably arranged to be offset with respect to one another.

The thickness of the wires or fibers is preferably less than 800 μm.

The above-described matrix and the wires and fibers permit the development of a fiber reinforced bone in the interface layer between implant and bone, thus assuring a firm physical bond between natural bone and implant in the resection plane.

As already described above, the artificial joint system may be composed of a shaft or a clamping device which can be screwed into the long bone or can be firmly anchored in the long bone by a wedge effect, an intermediate member and a sliding surface, the artificial joint head. Intermediate member and sliding surface may either be firmly connected to one another so as to be inseparable or separable, preferably by way of a screw connection or a taper.

If another type of clamping device (without shaft) is employed, such a device should preferably be composed of a plate which comes to rest against the cortex on the opposite side with respect to the resection plane and which has a central threaded bore or a plurality of small threaded bores into which can be screwed a threaded pin, with which the intermediate member is equipped and which is oriented perpendicularly to the resection plane.

To better fix the intermediate member in the remaining bone it is recommended to apply a plate to the contact face between the intermediate member and the respective bone, with such plate being adapted to the respective bone (also geometrically) and extending beyond the resection plane into the region of the spongy tissue.

If a shaft is used as part of a clamping device, pretension in the intermediate member can be realized by providing the shaft with a threaded bore which extends perpendicularly to the resection plane. At the head or foot of the shaft, a device is provided, preferably an internal or external hexagon, which permits easy screwing of the shaft in the long bone during surgery so as to permit it to be pretensioned. The shaft may either be made of a solid or perforated core which may itself be composed of metallic or composite fiber substances. A material that is resorbed more slowly than that of the intermediate member is employed for coating the shaft material. This has the advantage that the firm anchorage of the intermediate member is formed before the flow of forces ceases in the shaft.

Finally, the central interior bore provided in the core of the shaft and/or the penetrations provided in the jacket are preferably filled with a resorbable, bioactive and/or osteogenesis-inducing material.

An intermediate member is preferably implanted by means of a surgical instrument which corresponds to the outer contour of the intermediate member and which is equipped with a threaded pin oriented perpendicularly to the resection plane to be screwed into the threaded bore of the shaft for precise guidance.

BRIEF DESCRIPTION OF THE DRAWING

Embodiments of the invention are illustrated in the drawings. Shown in:

FIG. 2, is a cross-sectional view of a joint prosthesis implanted by means of a clamping device, and FIGS. 3 to 8, are sectional views of the shaft and parts of the intermediate member.

DESCRIPTION OF THE PREFERRED EMBODIMENTS

Figure 1:
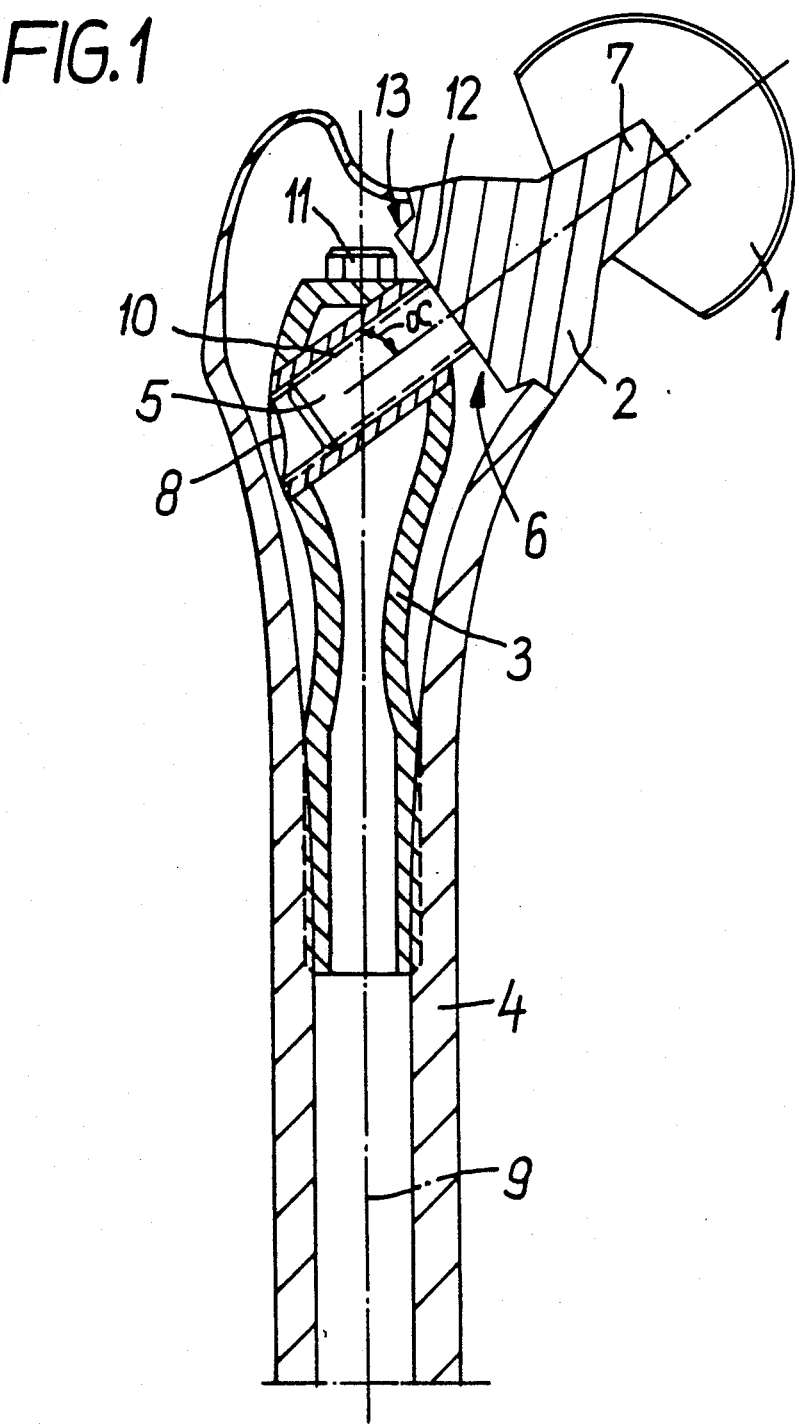
FIG. 1, is a cross-sectional view of an artificial joint implant having a shaft and inserted in a femur.

The artificial joint inserted in long bone 4 is composed of a shaft 3 and an intermediate member 2 (bone shaft section) screwed into shaft 3 by way of a threaded pin 5 at the intermediate member. On the side of intermediate member 2 facing away from resection plane 6, the intermediate member has a conical pin 7 on which is fastened, via a corresponding bore, the artificial joint head 1, the sliding surface. In its upper head region, shaft 3 has a threaded bore 8 which extends perpendicularly to resection plane 6. The threaded bore extends approximately at an angle $\alpha$ of 50° with respect to the common longitudinal axis of shaft 3 and long bone 4. In the present case, the angle is 53.5°. Pin 5 of intermediate member 2 has a threaded section 10 which corresponds to threaded bore 8. At the head of the shaft, an external hexagon 11 is provided which permits easy screwing of the shaft into the long bone during surgery. Moreover, shaft 3 is radially symmetrical and is provided with a central internal bore (not shown) and with perforations (not shown) in its jacket. Through the internal bore in shaft 3 and the jacket perforations, resorbable, bioactive and/or osteogenesis-inducing material, for example, spongy tissue in particular, can be filled into the shaft. The artificial joint system, in particular intermediate member 2 and shaft 3, are composed, on the side of the bone, of a wholly or partially resorbable matrix which is resorbed after implantation and replaced by natural bone. The artificial joint system is here composed either of a metallic material which, on the side of the bone, ends in a brush-like shape, or of a composite fiber material in which, likewise, part of the fiber end on the side of the bone ends in a brush-like shape. The wires or fibers which, on the side of the bone, end in a brush-like shape are fixed to the core material of the intermediate member or shaft. The bioactive or osteogenesis inducing substance introduced on the side of the bone into the interstices between these fibers or wires is wholly or partially resorbed by the body and is replaced by natural bone, with the bone growing completely and without interference around the individual fibers or wires, which are arranged in such a manner that they do not overlap or intersect one another, but stand, like porcupine quills, perpendicularly to the resection plane or at an angle optimized with respect to the resection plane. All fibers or groups of fibers are here parallel to one another.

In the interface layer between implant and bone, i.e. in resection plane 6, there now is produced a fiber reinforced bone which assures a firm physical bond between the natural bone and the implant.

Shaft 3 introduced into long bone 4 serves as a counterbearing for intermediate member 2 to produce the required pretension during the first phase after implantation. Shaft is preferably coated with resorbable bioactive and/or osteogenesis-inducing material; after the implantaton, the coating is resorbed by the body and enclosed by connective tissue to such an extent that the flow of forces under load existing in the first phase is gradually reduced. Ultimately, the forces flow exclusively an without interference through the resection plane. This is possible because, similar to the healing process of a bone fracture, a firm physical and/or chemical bond exists between the bone and intermediate member 2 at intermediate member 2 in resection plane 6.

The shaft itself may be composed either of a solid or a perforated core. The core of shaft 3 may be made of a metallic material as well as of a composite fiber material. A material which resorbs slower than that used for intermediate member 2 will preferably be used to coat the shaft material. The advantage of this is that a firm anchorage forms at intermediate member 2 before the flow of forces ceases in the shaft.

Intermediate member 2 is composed of a core of composite fiber material or of metallic material. Face 12 with which intermediate member 2 contacts resection plane 6 may be provided with additional macroscopic surface structures so as to increase the surface area. Contact face 12 is arranged with respect to the remaining bone so that the introduction of forces from the intermediate member of the implant into the remaining bone is effected perpendicularly. To better fix intermediate member 2 in the remaining bone, a plate or bulge 13 adapted to the bone in question and disposed in the spongy tissue region at contact face 12 of intermediate member 2 will be made of bioactive and/or osteogenesis inducing material or have the a structure described in the claims and below.

The artificial joint system illustrated in FIG. 2, which is introduced into long bone 4, like the joint system described in connection with FIG. 1, has an artificial joint head 1 as well as an intermediate member 2 equipped with a pin 5 having a thread 10. In contradistinction to the joint system according to FIG. 1, this system, however, employs a different type of clamping device which, in the present case, is composed of a plate 14 adapted to the surface of the bone and equipped with a threaded bore to accommodate pin 5. The clamping device employed here, instead of shaft 3 according to FIG. 1, for intermediate member 2 may be composed either of nonresorbable material which can be removed after the bone has grown into the intermediate member or it may be made of wholly or partially resorbable material.

In principle, the clamping systems may be composed of commercially available systems employed for healing of fractures or of special screw and/or wedge connections at the side opposite the cortex with respect to the resection plane. To provide a better fix, intermediate member 2 is provided with a plate 15 of bioactive and/or osteogenesis inducing material or with the already mentioned wires or fibers which are adapted to the contact face of the remaining bone in resection plane 6.

After appropriate preparation of long bone 4, which essentially includes producing the resection plane and a bore through bone 4 perpendicular to resection plane 6, intermediate member 2 is inserted into the bone. It is understood that for this purpose, a surgical instrument is employed which has an outer contour that corresponds to the contact face or to plate 15, respectively, of the intermediate member [in]resection plane 6.*

*Translator's note: Sentence grammatically unclear in German. Pin 5 of the intermediate member is then inserted into the prepared bore in the bone and is fixed by way of a clamping member 14, for which purpose pin 5 is advisably equipped with an internal or external hexagon at its free end 16. The threaded pin is tightened in such a manner that a defined pretension is realized between bone 4 and intermediate member 2 or contact plate 15, respectively. The sectional views of shaft or intermediate member portions facing the bone and shown in FIGS. 3 through 8 are provided with a special matrix 22 in which are contained the metallic wires or composite materials, which are durably anchored in the implant core and end, preferably perpendicularly to the implant surface, in a porcupine quill or brush-like manner.

FIG. 3 shows a metallic core 24 as well as cylindrical metal wires 21 which are fastened to the core surface at an interface layer 23 coated with an adhesive. Interstice 22 (the matrix) is filled with a wholly or partially resorbable, bioactive and/or osteogenesis-inducing material.

In contradistinction thereto, in the embodiment according to FIG. 4, wires 25 have a conical shape. In both embodiments, according to FIGS. 3 and 4, core 24 and wires are formed uniformly of a single material, metal in the present case.

In contrast thereto, in the embodiments according to FIGS. 5 to 7, different materials are involved; namely, metal on the one hand, and a composite material on the other hand. Thus, in the implant shown in FIG. 5, helical composite material fibers 26 are fastened to a metallic core 24. The implant according to FIG. 6 is additionally provided with a core 27 which is surrounded by a helix 28 of composite material that has a decreasing helix radius. This helix 28 as well as core 27 are both likewise fastened to the surface of the implant core.

It is possible to make core 27 and the helix 28 surrounding it of the same or different materials, with metals or composite materials being applicable in each case.

The implant shown in FIG. 4 is provided with helical metal wires 29 and 30, with the radius of the helix being uniform in the former case and becoming smaller with increasing distance from the implant core 24 in the latter case. In addition, it is also possible to employ helixes having different diameters or those whose pitch is greater than or equal to the respective helix diameter. In particular, metal wires 29 and 30 extend far into implant core 24 of composite material.

FIG. 8 finally shows pin-shaped fibers 31, each having a different length and each being fastened to an implant core of composite material.

Regardless of whether the wires or fibers in FIGS. 3 to 8 project from the implant surface in uniform or nonuniform spacing, individually or in groups, their spacing is selected so that bone tissue between them can be supplied without interference.

I claim:

1. An artificial joint system for cement-free implantation into a bone provided with a resection plane and a bore for accommodating at least a portion of the artificial joint system, the artificial joint system comprising:
   an implant comprised of an intermediate member having a contact face provided thereon, which contact face engages the resection plane of the bone when the artificial joint system is implanted therein, and having at least one pin positioned on and protruding from the contact face, which at least one pin has a threaded section; and
   a clamping device comprised of a shaft having defined therein at least one threaded bore for receiving and threadedly engaging the at least one pin, wherein the artificial joint system has a surface and is provided, along at least a portion of the surface thereof adjacent to the bone, with a transition structure, the transition structure comprising a matrix which is at least partially resorbable and a plurality of projecting members, which plurality of projecting members extend perpendicularly outwardly and away from said at least a portion of the surface of the artificial joint system adjacent to the bone, are one of flexible metallic wires and flexible fibers, are surrounded by and embedded in the matrix, have a shape which is one of a pin shape, a helical shape, and a wavy shape, and have a modulus of elasticity corresponding to the modulus of elasticity of the bone tissue which surrounds same when the artificial joint system is implanted.

2. The artificial joint system according to claim 1, wherein at least one of the shaft and the intermediate member has a core, which core is biocompatible and is made of one of a metallic material and a composite material, and wherein the plurality of projecting members are durably anchored to the core.

3. The artificial joint system according to claim 1, wherein the plurality of projecting members extend parallel to one another.

4. The artificial joint system according to claim 1, wherein each of the plurality of projecting members has a structure which permits each of the plurality of projecting members to exhibit a uniform tension and strength over its length.

5. The artificial joint system according to claim 1, wherein the plurality f projecting members are spaced apart from one another in an irregular pattern.

6. The artificial joint system according to claim 1, wherein the plurality of projecting members are spaced apart from one another and adjoining projecting members are separated by an interstice defined therebetween which is large enough to accommodate the growth of bone tissue therein.

7. The artificial joint system according to claim 6, wherein each said interstice is filled with said matrix selected from the group consisting of a material which is at least partially resorbable, a bioactive material, an osteogenesis-inducing material, and mixtures thereof.

8. The artificial joint system according to claim 1, wherein the plurality of projecting members have lengths which vary from one another.

9. The artificial joint system according to claim 1, wherein the plurality of projecting members have thicknesses which vary from one another.

10. The artificial joint system according to claim 1, wherein each of the plurality of projecting members has a wavy shape and the plurality of projecting members are arranged in an offset pattern with respect to one another.

11. The artificial joint system according to claim 1, wherein each of the plurality of projecting members has the form of a helix.

12. The artificial joint system according to claim 11, wherein each helix has a shape which is one of a cylindrical shape, a conical shape, and a parabolic shape, and a pitch which is at least equal to the thickness of each projecting member.

13. The artificial joint system according to claim 2, wherein the plurality of projecting members are flexible fibers, each flexible fiber being provided with an inner core which is fixedly attached to the core of said at least one of the shaft and the intermediate member, whereby shear forces are accommodated.

14. The artificial joint system according to claim 1, wherein each of the plurality of projecting members has a thickness of less than 800 μ.

15. The artificial joint system according to claim 2, wherein the plurality of projecting members which are durably anchored to the core by one of an adhesive means, welding, and sintering.

16. The artificial joint system according to claim 1, wherein at least a portion of the surface of the shaft is provided with a material which is one of a bioactive material and an osteogenesis-inducing material, which material is at least partially resorbable.

17. The artificial joint system according to claim 1, wherein the shaft and the intermediate member are at least coated with a first and a second resorbable material, respectively, and wherein the first resorbable material resorbs at a slower rate than that of the second resorbable material.

18. The artificial joint system according to claim 1, wherein the intermediate member is provided with means to facilitate threaded engagement of the pin and the threaded bore of the shaft so as to produce a pretension.

19. The artificial joint system according to claim 1, wherein the shaft has a longitudinal axis and a central internal bore provided therein, which central internal bore extends along the longitudinal axis of the shaft.

20. The artificial joint system according to claim 19, wherein a plurality of perforations are provided in the shaft.

21. The artificial joint system according to claim 20, wherein the perforations are filled with a material selected from the group consisting of a resorbable material, a bioactive material, and osteogenesis-inducing material, and mixtures thereof.

22. The artificial joint system according to claim 1, wherein at least one of the clamping device and the intermediate member are made, at least in part, of a material which is at least one of a bioactive material and an osteogenesis-inducing material, said material being selected from the group consisting of an inorganic material, an organic material, and mixtures thereof.

23. The artificial joint system according to claim 22, wherein said material is selected from the group consisting of tricalcium phosphate, hydroxylapatite, bioglass, a mixture of bioglasses, and mixtures thereof.

24. The artificial joint system according to claim 1, wherein at least one of the clamping device and the intermediate member is coated at least partially with a material which is at least one of a bioative material and an osteogenesis-inducing material.

25. The artificial joint system according to claim 1, wherein the implant further comprises an artificial joint head and wherein the intermediate member is connected to the artificial joint head by one of a screw connection and a taper connection.

26. The artifcial joint system according to claim 1, wherein the intermediate member having said contact face provided thereon has a central bore, which central bore permits bone tissue along the resection plane to grow into the intermediate member.

27. The artificial joint system according to claim 1, wherein the bone has a region of spongy tissue at least proximate to the resection plane thereof and wherein a contact plate is applied to the contact face, the contact plate having a transition structure provided along the surface thereof which engages the resection plane of the bone, the transition structure projecting beyond the resection plane into the spongy tissue region of the bone when the implant is implanted.

28. The artificial joint system according to claim 1, wherein the intermediate member having said contact face provided thereon has a longitudinal axis which extends perpendicularly to the contact face, and wherein the intermediate member is radially symmetrical about the longitudinal axis.

29. A method for implanting an artificial joint system for cement-free implantation into a bone provided with a resection plane and a bore for accommodatnng at least a portion of the artificial joint system, the method comprising:
providing an artificial joint system including an implant comprised of an intemediate member having a contact face provided thereon, which contact face engages the resection plane of the bone when the artificial joint system is implanted therein, and having at least one pin positioned on and protruding from the contact face, which at least one pin has a threaded section; and a clamping device comprised of one of a shaft and a plate, which one of a shaft and a plate is provided with at least one threaded bore for receiving and threadedly engaging the at least one pin, wherein the artificial joint system is provided, along at least a portion of the surface thereof adjacent to the bone, with a transition structure, the transition structure comprising a matrix which is at least partially resorbable and a plurality of projecting members which extend perpendicularly outwardly and away from said at least a portion of the surface of the artificial joint system adjacent to the bone, said projecting member are one of flexible metallic wires and flexible fibers, are surrounded by and are embedded in the matrix, have a shape which is one of a pin shape, a helical shape, and a wavy shape and have a modulus of elasticity corresponding to the modulus of elasticity of the bone tissue which surrounds same when the artificial joint system is implanted;
resting the contact face on the resection plane of the bone, which resection plane includes a bone cortex portion, so that the contact face rests medially on the cortex portion and engages same under pretension.

30. The method according to claim 29, further comprising
enclosing each of the plurality of projecting members with bone cells so as to connect same to one another with the bone cells, entirely free of connective tissue and without interruption.

31. An artificial joint system for cement-free implantation into a bone provided with a resection plane and a bore for accommodating at least a portion of the artificial joint system, the artificial joint system comprising:
an implant comprised of an intermediate member having a contact face provided thereon, which contact face engages the resection plane of the bone when the artificial joint system is implanted therein, and having at least one pin positioned on and protruding from the contact face, which at least one pin has a threaded section; and
a clamping device comprised of a plate having defined therein at least one threaded bore for receiving and threadedly engaging the at least one pin, wherein the artificial joint system is provided, along at least a portion of the surface thereof adjacent to the bone, with a transition structure, the transition structure comprising a matrix which is at least partially resorbable and a plurality of projecting members, which plurality of projecting members extend perpendicularly outwardly and away from said at least a portion of the surface of the artificial joint system, are one of flexible metallic wires and flexible fibers, are surrounded by and embedded in the matrix, have a shape which is one of a pin shape, a helical shape, and a wavy shape, and have a modulus of elasticity corresponding to the modulus of elasticity of the bone tissue which surrounds same when the artificial joint system is implanted.

* * * * *